US00PP24662P3

(12) United States Plant Patent
Brazelton et al.

(10) Patent No.: US PP24,662 P3
(45) Date of Patent: Jul. 22, 2014

(54) BLUEBERRY PLANT NAMED 'ZF06-179'

(50) Latin Name: ***Vaccinium angustifolium×corymbosum* hybrid**
Varietal Denomination: ZF06-179

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 150 days.

(21) Appl. No.: 13/385,905

(22) Filed: Mar. 12, 2012

(65) Prior Publication Data

US 2013/0239263 P1 Sep. 12, 2013

(51) Int. Cl.
*A01H 5/00* (2006.01)

(52) U.S. Cl.
USPC ..... Plt./157

(58) Field of Classification Search
CPC ..... A01H 5/08
USPC ..... Plt./157
See application file for complete search history.

*Primary Examiner* — June Hwu
(74) *Attorney, Agent, or Firm* — Davis Wright Tremaine LLP; Dale C. Hunt; Wenhua Yu

(57) ABSTRACT

The new blueberry plant variety 'ZF06-179' is provided. 'ZF06-179' is a cold hardy ornamental variety intended for nursery, landscape, and home garden use. The variety has a dwarf growing habit with attractive foliage that is light green with red tips throughout the growing season, turning to yellow and red in the fall. 'ZF06-179' ripens in mid-July and produces high quality, medium sized fruit. The plant has an estimated chilling requirement of 1000-1200 hours.

4 Drawing Sheets

Latin name of the family, genus, and species:
Family—*Ericaceae*
Genus—*Vaccinium*
Species—*angustifolium×corymbosum* hybrid
Variety denomination: The new blueberry plant claimed is of the variety denominated 'ZF06-179'.

CROSS REFERENCE TO RELATED APPLICATIONS

None.

STATEMENT REGARDING FEDERALLY-SPONSORED RESEARCH AND DEVELOPEMNT

None.

BACKGROUND OF THE INVENTION

The present invention relates to the discovery of a new and distinct cultivar of half-high blueberry (*Vaccinium angustifolium×corymbosum* hybrid) and referred to as 'ZF06-179', as herein described and illustrated.

The new blueberry plant variety 'ZF06-179' was selected in Lowell, Oreg. in 2006. 'ZF06-179' is a cold hardy ornamental variety intended for nursery, landscape, and home garden use. The variety has a dwarf growing habit with attractive foliage that is light green with red tips throughout the growing season, turning to yellow and red in the fall. 'ZF06-179' ripens in mid-July and produces high quality, medium sized fruit. The plant has an estimated chilling requirement of 1000-1200 hours.

Pedigree and History: The new blueberry plant originated from a 2003 controlled cross pollination of 'Tophat' (pollen parent, unpatented) by 'Polaris' (female parent, unpatented). The seedling was first selected from a high density field planting in the summer of 2006 at which time it was propagated by softwood cuttings. The selection was planted in replication in a test field in Lowell, Oreg. in the fall of 2007. Test plots were also established in Benton and Whatcom Counties in Washington, and in Kern and Ventura Counties in California in 2009. These plots have been observed carefully (from flowering through fruit ripening, leaf senescence and dormancy each year) and no mutations of off-type plants have been observed.

The new variety can be compared to unpatented male parent 'Tophat' in that 'ZF06-179' is more compact, and has red color on the tips of the leaves during the growing season.

The new variety can be compared to the unpatented female parent 'Polaris' in that 'ZF06-179' is a dwarf, bears smaller fruit, and has smaller, red tipped leaves.

The new variety can be compared to 'Chippewa', a cold hardy, half high variety. 'ZF06-179' differs from 'Chippewa' in that it is smaller in size, has smaller fruit and has red color on the tips of the leaves during the growing season.

The new blueberry plant variety 'ZF06-179' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'ZF06-179' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'ZF06-179':

1. A dwarf growing habit.
2. Light green leaves tipped with deep red throughout growing season.
3. Cold hardiness.
4. Foliage with bright yellow and red fall color.

BRIEF DESCRIPTION OF THE DRAWINGS

The accompanying photographic illustration shows typical specimens in full color of the foliage and fruit of the new variety 'ZF06-179'. The colors are as nearly true as is reasonably possible in a color representation of this type.

BOTANICAL DESCRIPTION

Figure 1:
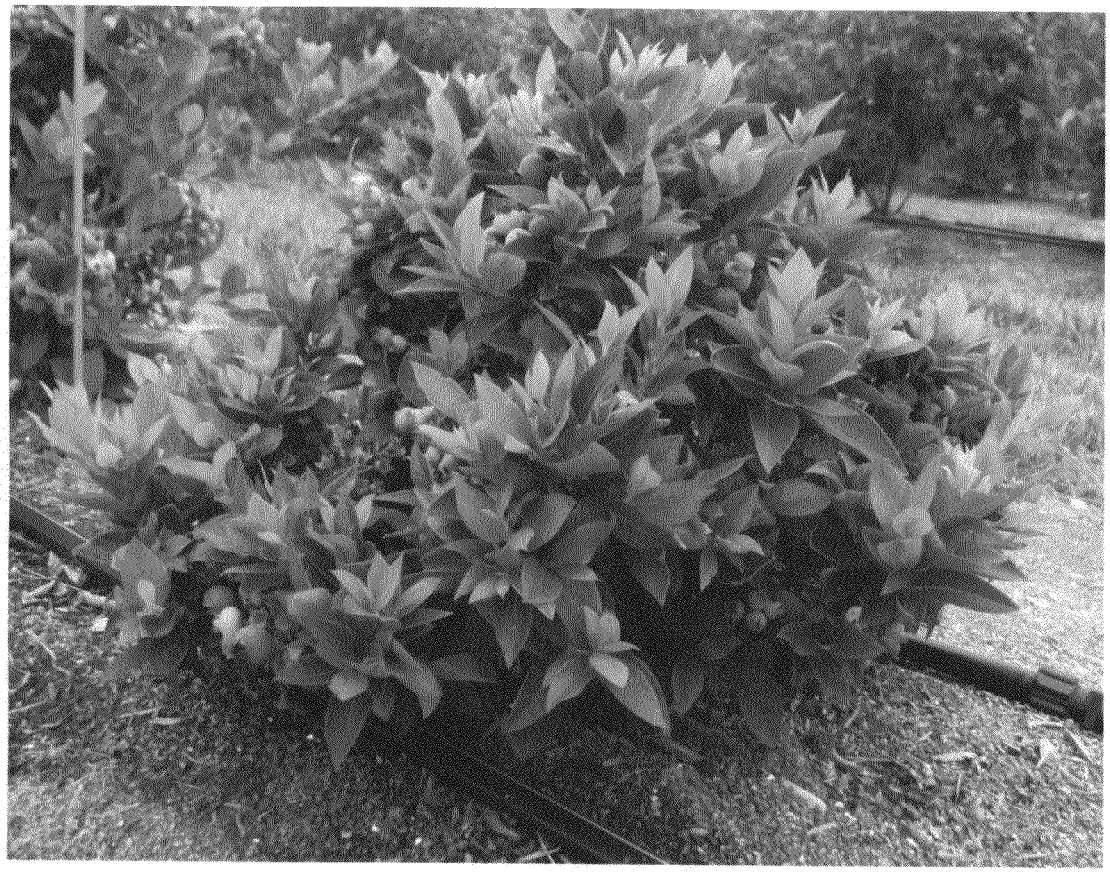
FIG. 1 is a photograph of the new variety 'ZF06-179', highlighting the plant's dwarf, compact growth habit and red tipped foliage.
Figure 2:
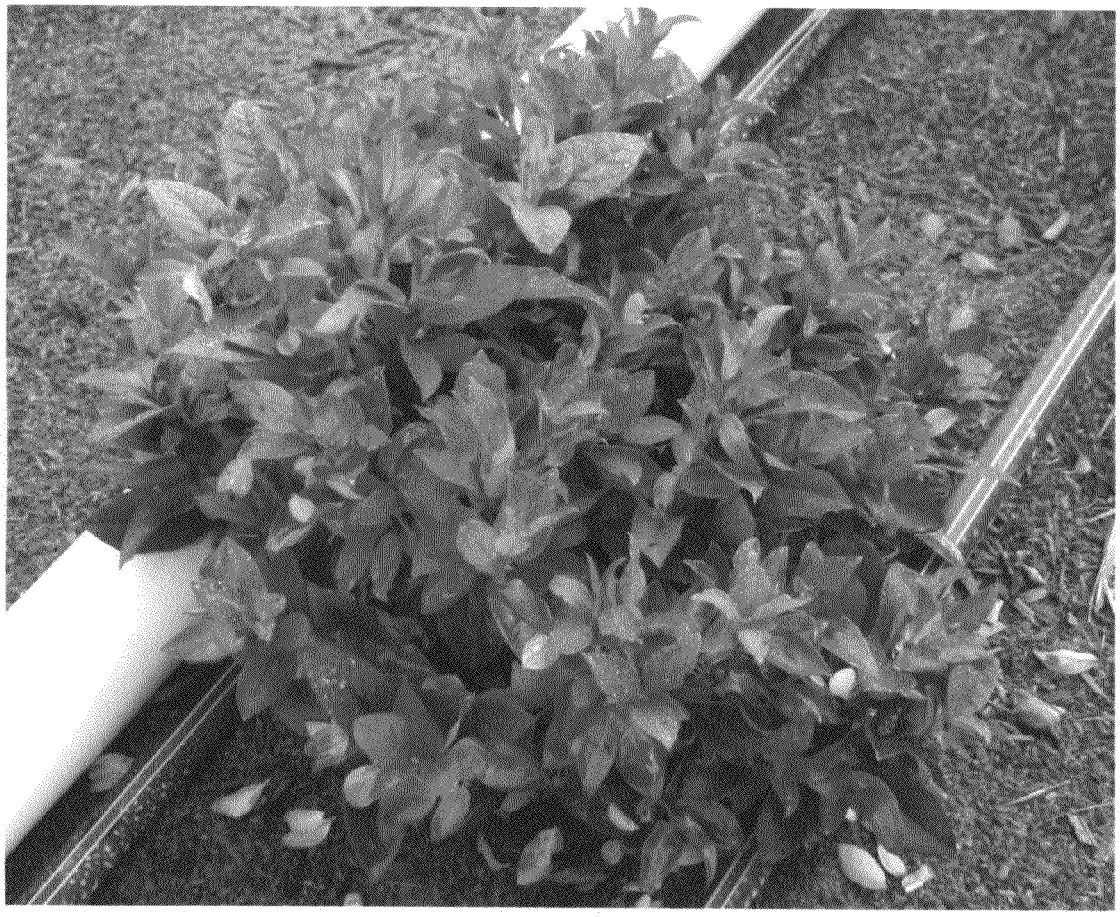
FIG. 2 is a photograph of the new variety 'ZF06-179', highlighting the plant's yellow and red fall foliage.
Figure 3:
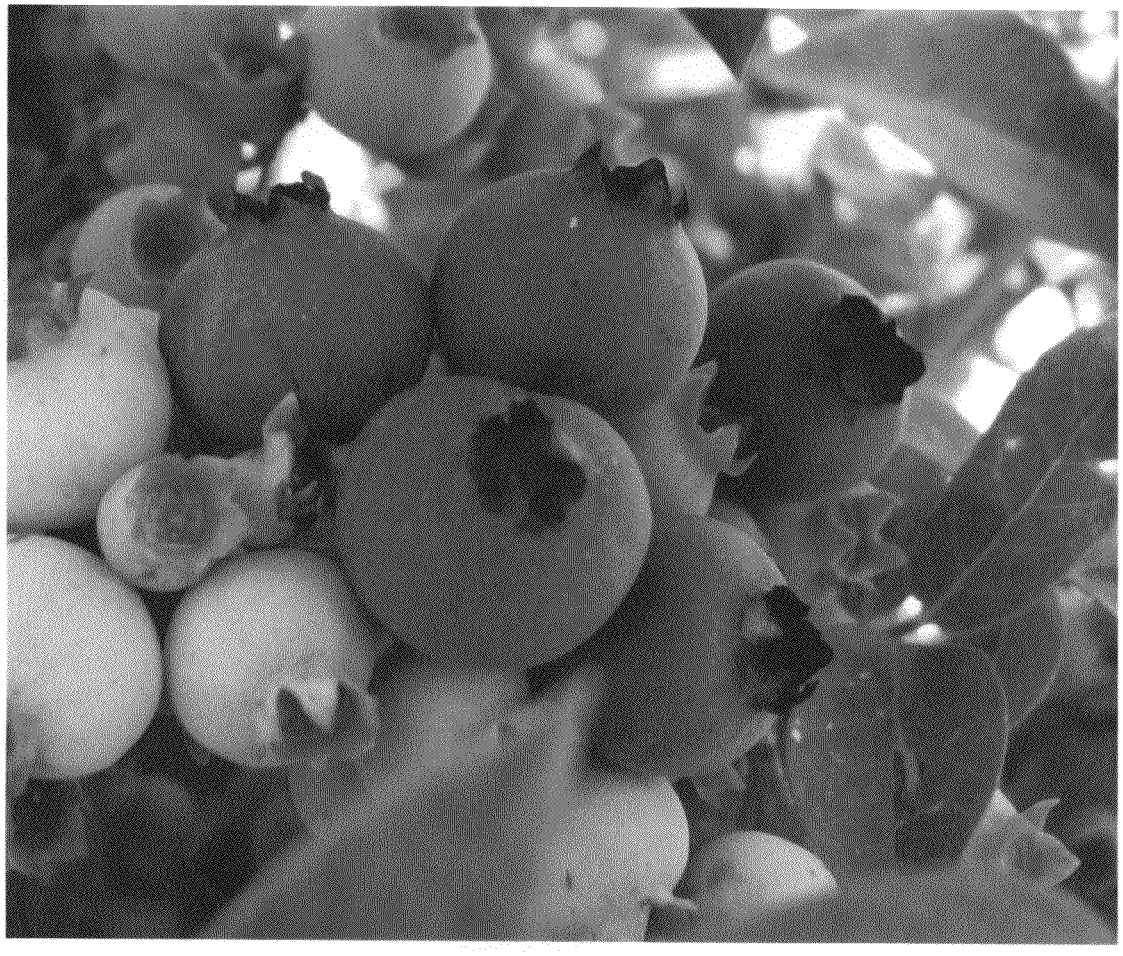
FIG. 3 is a photograph of the fruit of the new variety 'ZF06-179'.
Figure 4:
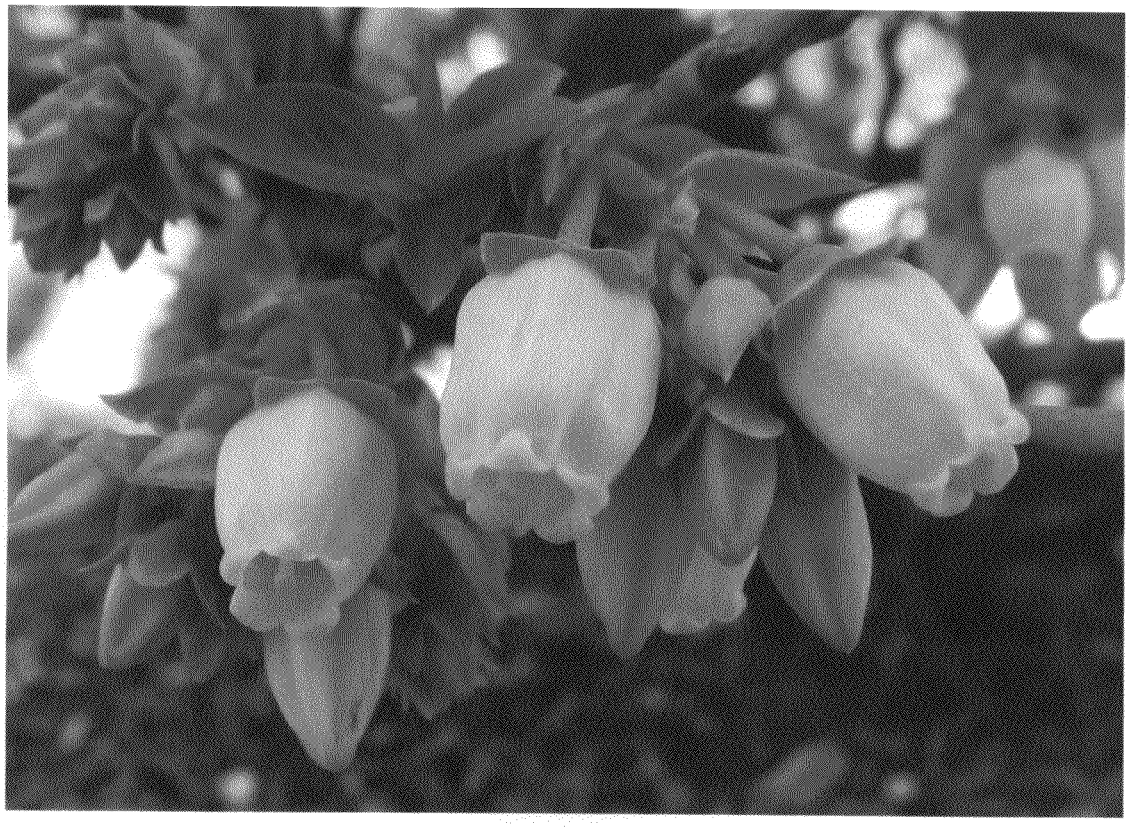
FIG. 4 is a photograph of the flowers of the new variety 'ZF06-179'.

The following detailed description sets forth the distinctive characteristics of 'ZF06-179'. The data which defines these characteristics was collected from asexual reproductions of the original selection. Dimensions, sizes, colors and other characteristics are approximations and averages set forth as accurately as possible. The plant history was taken on plants approximately three years of age, and the descriptions relate to plants grown in the field in Lowell, Oreg. Color designations are from "The Pantone Book of Color" (by Leatrice Eiseman and Lawrence Herbert; Harry N. Abrams, Inc., Publishers, New York, 1990). Where the Pantone color designations differ from the colors in the photographs, the Pantone colors are accurate.

Classification:

*a. Family.*—*Ericaceae.*
*b. Genus.*—*Vaccinium.*
*c. Species.*—*Angustifolium*×*corymbosum* hybrid.
*d. Common name.*—Half-high blueberry.

Parentage:

*Female parent.*—'Polaris' (unpatented).
*Male parent.*—'Tophat' (unpatented).

Market class: 'ZF06-179' is a dwarf ornamental blueberry variety intended for the nursery, landscape and home gardening market.

PLANT

Plant size: Very small

*a. Height.*—Average of 14 inches (35.56 cm).
*b. Canopy diameter.*—Average of 18 inches (45.72 cm).

Growth habit: Dwarf, round, compact habit.
Plant vigor: Good.
Twigginess: Low.
Evergreenness: Low in Lowell, Oreg.
Suckering: Low.
Chilling requirement: Approximately 1000 to 1200 hours of temperatures at or below 45° F. (about 7° C.).
Cold hardiness: Expected range of adaptability USDA Hardiness Zones 3-5.
Productivity: In Lowell, Oreg., the average per plant harvest weight on 3-year-old plants, is approximately 0.5 lbs (0.2268 kg).
Propagation: Easily propagated from softwood cuttings.
Disease resistance/susceptibility: Showed average to moderate susceptibility to Leaf rust (*Naohidemyces vaccinii*) in October, 2011. Did not appear to be susceptible to any other diseases or pests commonly seen at the trial location.
Survival: Good. Plants grow and survive well in both nursery and field settings.

TRUNK AND BRANCHES

Texture:

*a. Surface texture of new wood.*—Smooth.
*b. Surface texture of* 1 *year wood.*—Smooth.
*c. Surface texture of* 3 *year and older wood.*—Rough.

Color:

*a. Color of new wood.*—Pantone Raw Umber 17-1422.
*b. Color of bark at* 1 *year.*—Pantone Clay 15-1231.
*c. Color of bark* 3 *years and older.*—Pantone Clay 15-1231.

FOLIAGE

Internode length: Average of 4.5 mm.
Leaf dimensions:

*a. Leaf length* (*including petiole, from tip of petiole to end of blade*).—Average of 41.8 mm.
*b. Leaf width.*—Average of 19.9 mm.

Leaf shape: Elliptical with rounded base and acute apex.
Leaf margin: Entire.
Leaf color upper leaf surface:

*a. Mature leaf color.*—Pantone Grasshopper 18-0332.
*b. New leaf color.*—Pantone Peridot 17-0336, tips of new leaves Pantone Mineral Red 17-1537.

Leaf color lower leaf surface: Pantone Peridot 17-0336.
Fall leaf color: Pantone colors Daffodil 14-0850, Saffron 14-1064, Mineral Red 17-1537.
Petiole:

*a. Petiole length.*—Average of 2.8 mm
*b. Petiole surface texture.*—Smooth.
*c. Petiole surface color.*—Pantone Sweet Pea 15-0531.

Pubescence:

*a. Pubescence upper leaf surface.*—Absent.
*b. Pubescence lower leaf surface.*—Absent.
*c. Pubescence leaf margins.*—Absent.

Precocity: Flower bud break occurs prior to vegetative bud break. Flowers persist during initial vegetative growth period.

FLOWERS

Flower arrangement: Axillary raceme.
Flower shape: Cylindrical
Fragrance: Mild, sweet.
Flower bud density: Very high.
Flower length: Average of 9 mm.
Immature flower color: Pantone Snow White 11-0602.
Flowering period: In Lowell, Oreg., first flowers open in late March and continue through late May.
Flowering cluster: Loose.
Number of flowers: Average of 6-8 flowers per cluster.
Corolla:

*a. Corolla length.*—Average of 6.6 mm.
*b. Corolla diameter.*—Average of 4.3 mm.

*c. Corolla aperture*.—Average of 5.6 mm.
*d. Corolla surface texture*.—Smooth.
*e. Corolla color*.—Pantone Pastel Parchment 11-0603.

Flower peduncle:
*a. Peduncle length*.—Average of 7.5 mm.
*b. Peduncle color*.—Pantone Pinecone 19-1121.

Flower pedicel:
*a. Pedicel length*.—Average of 4.3 mm.
*b. Pedicel color*.—Pantone Tarragon 15-0326.

Calyx:
*a. Calyx diameter*.—Average of 4.2 mm.
*b. Calyx surface texture*.—Smooth.
*c. Calyx color*.—Pantone Peridot 17-0336; Wild Rose 16-1715, and Lilas 16-1708.

Style length: Average of 6.9 mm.
Pistil color: Pantone Mellow Green 12-0426.
Stigma location: Average of 0 to 0.2 mm beyond lip of corolla.

Anther:
*a. Anther length*.—Average of 2.5 mm.
*b. Anther color*.—Pantone Glazed Ginger 18-1154.

Pollen:
*a. Pollen abundance*.—Medium.
*b. Pollen staining*.—95% fertile, staining using 2% acetocarmine stain.
*c. Pollen color*.—Pantone Pale Banana 12-0824.

Self compatibility: Moderate. On average, 75% of flowers manually self pollinated reached maturity.
Average inflorescence size: 20.8 mm

FRUIT

Mean harvest date first pick: July 24.
Mean date of mid harvest: July 31.
Mean harvest date last pick: August 10.

Calyx:
*a. Calyx aperture*.—Average of 4.6 mm on a mature berry.
*b. Calyx lobes*.—Small on a mature berry.
*c. Calyx depth*.—Average of 0.89 mm.

Pedicel:
*a. Pedicel length*.—Average of 7.8 mm on ripe berry.
*b. Pedicel surface texture*.—Smooth.
*c. Pedicel scar*.—Small dry scar, averaging 1.9 mm in diameter.

Peduncle:
*a. Peduncle length*.—Highly variable, Average of 12.4 mm on ripe berry.
*b. Peduncle surface texture*.—Smooth.

Berry detachment: Medium to low detachment force on ripe berries.
Berries per cluster: Average of 5-7 berries per cluster.
Berry cluster (tight, medium or loose): Medium.
Berry weight: Average of 1.3 g.
Berry height: Average of 10.5 mm.
Berry width: Average of 14.6 mm.
Berry shape: Globose.

Berry color:
*a. Unripe berry color*.—Pantone Lettuce Green 13-0324.
*b. Mature berry color on plant*.—Pantone Blue Ice 17-3922.
*c. Berry color after harvest*.—Pantone Gray Dawn 14-4106.
*d. Berry color after polishing*.—Pantone Majolica Blue 19-4125.

Berry flesh color: Pantone White Jade 12-0315.
Surface wax: Light surface wax, with moderate persistence during handling of berry.
Berry firmness: Medium.
Berry flavor: Juicy berry with a balance between sweet and tart.
Berry texture: Good; smooth textured, juicy berry.

SEEDS

Seed color: Pantone Carob Brown 18-1229.
Seed weight: Average of 0.5 mg.
Seed length: Average of 1.7 mm.
Seed width: Average of 1.23 mm.
Seeds per berry: Average of 10 seeds per berry.

The invention claimed is:

1. A new and distinct variety of blueberry plant named 'ZF06-179', substantially as illustrated and described herein.

* * * * *